United States Patent [19]

Kellner et al.

[11] Patent Number: 5,068,473
[45] Date of Patent: Nov. 26, 1991

[54] HYDROGENOLYSIS/DEHYDROHALOGENATION PROCESS

[75] Inventors: Carl S. Kellner; V. N. Mallikarjuna Rao; Frank J. Weigert, all of Wilmington, Del.

[73] Assignee: E. I. du Pont de Nemours and Company, Wilmington, Del.

[21] Appl. No.: 596,551

[22] Filed: Oct. 17, 1990

Related U.S. Application Data

[63] Continuation of Ser. No. 305,698, Feb. 3, 1989, abandoned.

[51] Int. Cl.$^5$ ............... C07C 17/24; C07C 17/34; C07C 19/08; C07C 21/13
[52] U.S. Cl. ............... 570/176; 546/345; 570/143; 570/156
[58] Field of Search ............... 570/143, 156, 176

[56] References Cited

U.S. PATENT DOCUMENTS

| | | | |
|---|---|---|---|
| 2,615,925 | 10/1952 | Bordner | 260/653 |
| 2,697,124 | 12/1954 | Montell | 570/156 |
| 2,774,799 | 12/1956 | Montell et al. | 570/156 |
| 2,942,036 | 6/1960 | Smith et al. | 260/653 |
| 3,043,889 | 7/1962 | Smith et al. | 260/653.5 |
| 3,505,417 | 4/1970 | Gardner | 260/653.5 |
| 3,636,173 | 1/1972 | Gardner | 260/653.5 |
| 4,319,060 | 3/1982 | Cunningham et al. | 570/177 |

FOREIGN PATENT DOCUMENTS

| | | |
|---|---|---|
| 655397 | 1/1963 | Canada. |
| 164954 | 12/1985 | European Pat. Off.. |
| 134601 | 12/1977 | German Democratic Rep.. |
| 11-28942 | 5/1989 | Japan. |
| 698386 | 10/1953 | United Kingdom. |
| 1578933 | 11/1980 | United Kingdom. |

OTHER PUBLICATIONS

C. Gervasutti et al., J. Flourine Chem., 19, 1 (1981).

Primary Examiner—J. E. Evans

[57] ABSTRACT

A process for the hydrogenolysis and/or dehydrohalogenation of fluorohalocarbons and/or fluorohalohydrocarbons by reacting the fluorohalocarbons and/or fluorohalohydrocarbons with a source of hydrogen in the presence of a catalyst, the improvement comprising utilizing a rhenium-containing catalyst, which may, optionally, contain at least one Group VIII metal and may, optionally, be supported.

30 Claims, No Drawings

HYDROGENOLYSIS/DEHYDROHALOGENATION PROCESS

This application is a continuation-in-part continuation of application Ser. No. 07/305,698 filed Feb. 3, 1989, now abandoned.

FIELD OF THE INVENTION

Improved process for the hydrogenolysis and/or dehydrohalogenation of fluorohalocarbons and/or fluorohalohydrocarbons utilizing a rhenium catalyst.

BACKGROUND OF THE INVENTION

U.S. Pat. No. 2,615,925 claims a process for producing a fluoroolefin by passing a mixture containing a chlorofluoro-compound over a metallic copper catalyst at 460° to 700° C. In an example 1,1,1,2-tetrachloro-2,2-difluoroethane and hydrogen were passed over a copper catalyst at 370° C. to 390° C. to obtain a 72% yield of 1,1-dichloro-2,2-difluoroethylene.

GB 698,386 discloses a process for making $CClF=CF_2$ by passing a mixture of $CCl_2FCClF_2$ (CFC-113) and hydrogen through an empty reactor at 450° to 650° C., or for higher efficiency through a reactor charged with a catalyst containing nickel, copper, cobalt, platinum, or palladium, either supported on carbon or unsupported, at 375° to 525° C. $CClF=CF_2$ was produced in 52% yield while the major byproduct, $CF_2=CHF$ was produced in 5% yield.

U.S. Pat. No. 2,942,036 discloses a process for the reaction of $CF_3CCl_2CClF_2$ (CFC-215aa) with hydrogen over a palladium/carbon catalyst at 175°-350° C. to recover a product stream containing about 10% $CF_3CCl=CF_2$, about 15-16% $CF_3CH=CF_2$, about 60% $CF_3CH_2CHF_2$, and about 6-7% unreacted CFC-215aa.

U.S. Pat. No. 3,043,889 discloses a process for making $CClF=CF_2$ from CFC-113 and hydrogen by passing the mixture over a chromium oxide catalyst at 475°-550° C. Per pass conversions of CFC-113 of 15-30% were observed (col. 6, lines 17-30).

CA 655,397 claims a process for making $CHF=CF_2$ in larger amounts than $CH_2FCHF_2$ from CFC-113 by passing a mixture of hydrogen and CFC-113 over a Pd/C catalyst. The production of $CClF=CF_2$ is inhibited by adjusting the mol ratio of $H_2$/CFC-113 to be in the range of 0.7–1.7. In a typical example, CFC-113 and hydrogen at 265° C. are passed over a 1%Pd/C catalyst to obtain a 38% conversion to $CHF=CF_2$ and a 25% conversion to $CH_2FCHF_2$.

U.S. Pat. No. 3,505,417 discloses a process for the dehydrohalogenation of fluorohalocarbons using hydrogen over a catalytic composition consisting essentially of aluminum fluoride and at least one metallic element selected from groups I through VIII of the periodic table. The catalysts can also contain at least one metallic element which does not adversely affect their activity; some examples of which include: magnesium, barium, copper, sodium, potassium, chromium, nickel, molybdenum, vanadium, zinc, tin, silver, tungsten, iron, indium, titanium, germanium, platinum, palladium, rhodium, rhenium, osmium, and iridium. The patent claims a process for the dehydrohalogenation of fluorohalocarbons in the presence of hydrogen and a catalytic composition consisting of aluminum fluoride and from 0.05–30 weight percent of at least one of CuO, $Cr_2O_3$, $RhCl_3$, CoO, and Pt at 200°-600° C. When 1,2-dichloro-1,1,2,2-tetrafluoroethane (CFC-114) and hydrogen were passed over a copper oxide-cobalt oxide on fluorinated alumina catalyst, a 95% conversion of CFC-114 with a 78% yield of tetrafluoroethylene was obtained (Example 2).

U.S. Pat. No. 3,636,173 discloses a process and catalysts for the dehydrohalogenation of fluorohalocarbons using hydrogen and a catalytic composition containing aluminum fluoride and preferably a Group I-B, II-B, VI-B or Group VIII metal phosphate. Catalysts containing nickel or chromium phosphate are especially preferred. When CFC-113 and hydrogen were passed over a nickel phosphate catalyst at 385° C., a 98% conversion of CFC-113 with a 54% yield of chlorotrifluoroethylene was obtained (col. 5, lines 40–48).

GB 1,578,933 discloses a process for the manufacture of $CF_3CH_2F$ (HCF-134a) or $CHF_2CHF_2$ (HFC-134) by the hydrogenolysis of an appropriate haloethane over a hydrogenation catalyst. Palladium supported on carbon or alumina are specifically claimed. In Ex. 3 a 94% conversion of $CF_3CFCl_2$ (CFC-114a) with a 76% selectivity to HFC-134a and a 6.5% selectivity to $CF_3CFHCl$ (HCFC-124/$CF_2HCF_2Cl$ (HCFC-124a) for the hydrogenolysis of CFC-114a over a Pd/C catalyst at 310° C. is described.

C. Gervasutti et. al., J. Fluorine Chem., 19. 1 (1981) disclose the preparation of HFC-134a from the dichlorotetrafluoroethanes catalyzed by Pd/C to HFC-134a, $CF_3CH_3$ (HFC-143a) and HCFC-124 with a selectivity of 77.8%, 12.6% and 9.7% respectively.

U.S. Pat. No. 4,319,060 discloses a process for producing $CF_2ClCF_2Cl$ (CFC-114) substantially free of CFC-114a by the selective hydrogenolysis of a feed stream containing 0.1 to 25 weight percent of CFC-114a and 75 up to less than 100 weight percent of CFC-114 over a supported precious metal catalyst at 100°-300° C.

EP 164,954 discloses a method for the preparation of $CF_3CHFCl$ (HCFC-124) from $CF_3CFCl_2$ (CFC-114a) using an alkali metal amalgam in an active hydrogen containing (e. g., an alcohol) liquid medium.

The art shows that numerous catalysts, some of which are described above, for the hydrogenolysis and/or dehydrohalogenation of fluorohalocarbons are known. From the selectivities achieved in the art cited above, it is clear that there is a need for more selective catalysts. This need is particularly great because the products of these reactions are useful as environmentally desirable compounds for use as solvents, blowing agents and, particularly, refrigerants.

An object of this invention is to provide a process having improved selectivity and high conversion to the desired products.

SUMMARY OF THE INVENTION

This invention provides for an improvement in the process for the hydrogenolysis and/or dehydrohalogenation of fluorohalocarbons and/or fluorohalohydrocarbons by reacting the fluorohalocarbons and/or fluorohalohydrocarbons with a source of hydrogen in the presence of a catalyst. The improvement comprises utilizing a rhenium-containing catalyst.

The products of the improved hydrogenolysis and/or dehydrohalogenation can be obtained with combined selectivities of at least 90%. In addition, the rhenium-containing catalyst used in the practice of this invention is lower in cost than conventionally used noble metal catalysts and may also be more resistant to catalyst poisoning.

DETAILS OF THE INVENTION

The rhenium-containing catalyst useful in the practice of this invention may, optionally, contain a minor proportion of metals from Group VIII of the periodic table, e.g., Pt, Pd, Ru or Rh. The rhenium-containing catalyst may, or may not be supported. When not supported and combined with other metals, the amount of rhenium is at least 50% by weight, the balance being at least one selected from Group VIII metals.

The rhenium-containing material used to prepare the catalyst may be selected from rhenium metal; an organometallic rhenium compound, e.g. cyclopentadienylrhenium tricarbonyl; perrhenic acid; rhenium carbonyl; rhenium (III or IV) or chloride, or rhenium (IV, VI, or VII) oxide. The other metals, which may be added to the catalysts are those from Group VIII, e.g. Pt, Pd, Ru or Rh. The metal may be added in any form known to the art e.g., as a soluble salt of the metal.

The rhenium-containing catalyst may be supported on carbon, alumina, fluorided alumina, aluminum fluoride, calcium fluoride, or other supports, with carbon being the most preferable. The fluorided alumina can be prepared from either aluminum chloride or alumina by treatment with HF or a fluorine containing compound as is well known in the art. Alumina containing rhenium and, optionally, Group VIII metals may also be fluorided by treatment with HF or a fluorine-containing compound to produce the rhenium-containing catalyst. The aluminum chloride derived support may be an aluminum chlorofluoride, while the alumina derived support may contain oxyfluorides, hydroxyfluorides, and unreacted alumina.

The supported catalysts of the instant invention can be prepared by impregnating the support material with a solution of the rhenium-containing material and also, optionally, with solutions of Group VIII-containing materials. The concentration of rhenium on the support can range from 0.1% to 20% by weight. The concentration of Group VIII metals on the support can range from 0% to 10% by weight, but rhenium is always the major component.

The invention is applicable to the hydrogenolysis and/or dehydrohalogenation of fluorohalocarbons and/or fluorohalohydrocarbons that contain one or more fluorine atoms in the molecule. The fluorohalocarbons and/or fluorohalohydrocarbons are preferably those wherein halo is chloro or bromo. Included are fluorohalocarbons and fluorohalohydrocarbons composed, respectively of: carbon, chlorine, and/or bromine and fluorine; and carbon, hydrogen, chlorine and/or bromine and fluorine. The fluorohalocarbons and/or fluorohalohydrocarbons may contain 1 to 10 carbon atoms, preferably 1 to 4 carbon atoms. The fluorohalocarbons and/or fluorohalohydrocarbons include cyclic as well as acyclic compounds represented by the empirical formula $C_nH_mF_pX_q$, where X is Cl and/or Br, preferably Cl, and n is an integer from 1 to 10, m is an integer from 0 to 20, p is an integer from 1 to 21, and q is an integer from 1 to 21, provided that $m+p+q=2n+2$ when the compound is acyclic and equals $2n$ when the compound is cyclic.

In a preferred embodiment the fluorohalocarbons and/or fluorohalohydrocarbons are represented by the above empirical formula where n=1 to 4, m is 0 to 8, p is 1 to 9, and q is 1 to 9.

The fluorohalocarbons and/or fluorohalohydrocarbons also include aromatic compounds represented by the formula, $C_6H_nF_pX_a$, where X is Cl and/or Br, preferably Cl, and n is an integer from 0 to 4, p is an integer from 1 to 5, and q is an integer from 1 to 5, provided that $n+p+q=6$ and that when p=5, n=0; or by the formula $C_5NH_nF_pX_q$, where X is Cl and/or Br, preferably Cl, and n is an integer from 0 to 3, p is an integer from 1 to 4, and q is an integer from 1 to 4, provided that $n+p+q=5$ and that when p=4, n=0.

The products of the hydrogenolysis and/or dehydrohalogenation reactions of the $C_1$ fluorohalocarbons or fluorohalohydrocarbons may contain one to two hydrogen atoms and those from $C_2$ compounds from one to three hydrogen atoms with those containing one for the one carbon species and two to three for the two carbon species being preferred. The $C_3$ fluorohalocarbons or fluorohalohydrocarbons hydrogenolysis products may contain one to five hydrogen atoms with those containing one or four being preferred. In a similar manner the $C_4$ to $C_{10}$ hydrogenolysis products may contain one or more hydrogen atoms. It is to be understood that some or all of the reaction products from $C_2$ to $C_{10}$ may contain saturated or unsaturated carbon-carbon bonds.

A particularly desirable feature of utilizing the rhenium-containing catalyst in accordance with this invention is that the products of the hydrogenolysis and/or dehydrohalogenation will contain in high selectivity just one less chlorine than was present in the starting material.

The reaction temperature can range from about 100° C. to about 400° C. A preferred range is about 150° C. to about 350° C.

The amount of hydrogen contained in the gas stream contacted with the gaseous fluorohalocarbon and/or fluorohalohydrocarbon should be at least 0.2 moles per mole of fluorohalocarbon and/or fluorohalohydrocarbon and preferably from 0.5 to 5 moles.

Hydrogen can be fed either in the pure state or diluted with an inert gas, e.g., nitrogen, helium, or argon.

While vapor phase reactions are preferred, the catalysts may also be used for liquid phase hydrogenolysis reactions.

The products, consisting of either pure fluorohalocarbons or fluorohalohydrocarbons or mixtures of fluorohalocarbons and fluorohalohydrocarbons and a hydrogen halide, can be separated and purified by conventional means such as distillation.

A key feature of this invention is that through catalyst selection and, optionally, process control, such as variation of $H_2$/organic ratios, space velocity, pressure and temperature, a desired fluorocarbon may be obtained as a major product with high selectivity and minimal formation of unwanted by-products.

The fluorohalocarbons and/or fluorohalohydrocarbons utilized in the process of this invention are either commercially available or can be prepared by known methods.

The hydrogenolysis reactions may be conducted in any suitable reactor, including fixed and fluidized bed reactors. The reaction vessel should be constructed of materials which are resistant to the corrosive effects of hydrogen halide such as Hastelloy ® alloy or Inconel ® alloy.

Pressure is not critical. Atmospheric pressure is preferred for dehydrohalogenation and atmospheric or superatmospheric pressures for hydrogenolysis.

The products of these reactions may be used as solvents, blowing agents, refrigerants, propellants, and polymer intermediates.

EXAMPLES

All parts and percentages are by weight and all temperatures are degrees Celsius, unless otherwise noted. The following examples serve to illustrate the invention but they are not intended to limit it thereto.

GENERAL PROCEDURE

A designated quantity of catalyst was charged to a 1 cm diameter×10 cm length Vycor ® reactor, which was heated in a tube furnace. Hydrogen and a fluorohalocarbon or a fluorohalohydrocarbon vapor, or liquid fluorohalocarbon or fluorohalohydrocarbon which was vaporized in a preheated zone, were passed over the catalyst at the designated temperatures, flow rates, and at atmospheric pressure except for Examples 1, 4, 10, and 11, which were done at 740, 846, 155, and 155 kPa respectively. The reactor effluent was passed directly into a gas chromatograph equipped with a flame-ionization detector. Examples, 1, 3, 4, 10, and 11 were conducted in a 316 stainless steel reactor placed in a fluidized sand bath. The catalyst was loaded into the reactor and purged with $N_2$ followed by a $H_2$ purge. The temperature was then increased from room temperature to 300° or 350° C. at 0.5 ° C./min, held at maximum temperature, under hydrogen, for two hours, followed by cooling to the desired temperature for the reaction. The reactor effluent was analyzed as above. All percentages are area percent except Examples 1, 4, 10, and 11, where they are mol percent.

A 5% Re/C catalyst was prepared by adding calcined carbon granules (50 g, 20–50 mesh) to a rhenium heptoxide solution (33 mL of a 0.2 molar solution) which was further diluted with distilled water (52 mL). The granules were stirred occasionally and kept at room temperature for three hours. They were then dried at 110° C. in air for 18 hours followed by one hour at 150° C. in helium (100 cc/min), and one hour with a 1/1 He/$H_2$ mixture (200 cc/min). The temperature was then raised to 300° C. while passing the He/H2 mixture over it and maintained for 3 hours. Finally the catalyst was cooled to room temperature and passivated with 1.5% oxygen in nitrogen for 18 hours.

EXAMPLE 1

1,1,1-Trichloro-2,2,2-trifluoroethane (CFC-113a)

Hydrogenolysis

The catalyst was 5% Re/C (1.2 g) and the flow rates of $H_2$ and CFC-113a were 7.6 cc/min and 2 mL/h respectively and the reactor temperature was 202° C. After 59 hours of operation, CFC-113a conversion was 20% and selectivity to $CF_3CHCl_2$ was 96%.

The Re/C catalyst as used herein is preferred for hydrogenolysis of CFC-113a, because when a Re/Alumina catalyst was utilized under similar reaction conditions, a significant quantity of $CF_3CCl=CClCF_3$ was produced at the expense of the desired $CF_3CHCl_2$.

COMPARATIVE EXAMPLE A 1,1,1-Trichloro-2,2,2-trifluoroethane (CFC-113a)

Hydrogenolysis

The catalyst was 0.5% Pd/C (1.2 g) and the flow rates of $H_2$ and CFC-113a were 7.6 cc/min and 2 mL/h, respectively. The reaction temperature was 118° C. The following results were obtained by gas chromatographic analysis; 48% conversion of CFC-113a with the following selectivities, 10% $CF_3CHCl_2$, % $CF_3CH_2Cl$ and 33% $CF_3CH_3$. The rhenium based catalyst is seen to be far more selective for the removal of only one chlorine atom.

EXAMPLE 2

1,1,2-Trichloro-1,2,2-trifluoroethane (CFC-113)

Hydrogenolysis

The catalyst was 5% Re/$Al_2O_3$ (2.0 g) and the flow rates of $H_2$ and CFC-113 were 10 cc/min and 1 mL/h respectively. Hydrogenolysis results are shown in Table 1.

TABLE 1

| Run No. | Temp. °C. | $CF_2ClCFCl_2$ % Conv. | $CF_2ClCFHCl$ % Sel. | $FClC=CF_2$ % Sel. |
|---|---|---|---|---|
| 1 | 210 | 5 | 50 | 50 |
| 2 | 282 | 30 | 71 | 29 |
| 3 | 325 | 78 | 78 | 15 |

EXAMPLE 3

CFC-113 Dehydrohalogenation

The catalyst was 5% Re/C (2.6 g) and the flow rates of $H_2$ and CFC-113 were 6 cc/min and 2 mL/h respectively. Dehydrohalogenation results are shown in Table 2.

TABLE 2

| Run No. | Temp. °C. | $CF_2ClCFCl_2$ % Conv. | $CF_2ClCFHCl$ % Sel. | $ClFC=CF_2$ % Sel. |
|---|---|---|---|---|
| 1 | 200 | 15 | 5 | 95 |
| 2 | 250 | 91 | 20 | 80 |
| 3 | 300 | 78 | 11 | 85 |

EXAMPLE 4

1,1-Dichloro-1,2,2,2-tetrafluoroethane (CFC-114a)

Hydrogenolysis

The catalyst was 5% Re/C (1.2 g) and the flow rates of $H_2$ and CFC-114a were 7.6 cc/min and 1 mL/h respectively, and the reactor temperature was 253° C. Hydrogenolysis results are shown in Table 3.

TABLE 3

| Run Time Hrs. | Temp. °C. | $CH_3CFCl_2$ % Conv. | $CF_3CFHCl$ % Sel. | $CF_3CH_2F$ % Sel. | $CF_3CH_3$ % Sel. | Other[1] % Sel. |
|---|---|---|---|---|---|---|
| 10.6 | 253 | 61 | 81 | 0.5 | 1 | 16 |
| 18.3 | 253 | 54 | 82 | 0.5 | 1 | 15 |

[1]The major components are $CF_3CH=CHCF_3$ and $FClC=CF_2$.

EXAMPLE 5

CFC-114a Hydrogenolysis

The catalyst was 1% Pd/4% Re/C (0.2 g) and the flow rates of $H_2$ and CFC-114a were 11 cc/min and 5 cc/min respectively. Hydrogenolysis results are shown in Table 4.

COMPARATIVE EXAMPLE B 1,1-Dichloro-1,2,2,2-tetrafluoroethane (CFC-114a)

Hydrogenolysis

The catalyst was 0.5% Pd/C (0.2 g) and the flow rates of $H_2$ and CFC-114a were 12.5 cc/min and 2 mL/h, respectively. The reaction temperature was 225° C. The following results were obtained by gas chromatographic analysis; 67% conversion of CFC-114a with the following selectivities, 14% $CF_3CFHCl$, 78% $CF_3CH_2F$ and 7% $CF_3CH_3$. The rhenium based catalyst is seen to be far more selective for the removal of only one chlorine atom.

TABLE 4

| Run No. | Temp. °C. | $CF_3CFCl_2$ % Conv. | $CF_3CFHCl$ % Sel. | $CF_3CH_2F$ % Sel. | $CF_3CH_3$ % Sel. |
|---|---|---|---|---|---|
| 1 | 197 | 46 | 77 | 16 | 7 |
| 2 | 216 | 69 | 77 | 16 | 7 |
| 3 | 242 | 88 | 74 | 17 | 9 |
| 4 | 266 | 95 | 67 | 17 | 11 |
| 5 | 297 | 98 | 54 | 21 | 16 |
| 6 | 327 | 98 | 35 | 28 | 25 |

EXAMPLE 6

1,2-Dichloro-2,2,2-trifluorethane (HCFC-123)

Hydrogenolysis

The catalyst was 5% Re/C (2 g) and the flow rates of $H_2$ and HCFC-123 were 11 cc/min and 1 mL/h respectively. Hydrogenolysis results are shown in Table 5.

TABLE 5

| Run No. | Temp. °C. | $CF_3CHCl_2$ % Conv. | $CF_3CH_2Cl$ % Sel. | $CF_3CH_3$ % Sel. |
|---|---|---|---|---|
| 1 | 211 | 44 | 91 | 1 |
| 2 | 240 | 87 | 90 | 5 |
| 3 | 254 | 99 | 92 | 5 |

EXAMPLE 7

1-Chloro-1,2,2,2-tetrafluoroethane (HCFC-124)

Hydrogenolysis

The catalyst was 5% Re/C (1 g) and the flow rates of $H_2$ and HCFC-124 were 6 cc/min and 5 cc/min respectively. Hydrogenolysis results are shown in Table 6.

TABLE 6

| Run No. | Temp. °C. | $CF_3CHFCl$ % Conv. | $CF_3CH_2F$ % Sel. | $CF_3CH_3$ % Sel. |
|---|---|---|---|---|
| 1 | 280 | 9 | 53 | 44 |
| 2 | 321 | 24 | 40 | 54 |
| 3 | 360 | 48 | 31 | 62 |

EXAMPLE 8

1,3,3,3-Hexafluoro-2,2-dichloropropane (CFC-216aa)

Hydrogenolysis

The catalyst was 5% Re/A1203 (2.0 g) and the flow rates of $H_2$ and CFC-216aa were 5 cc/min and 1 mL/h respectively. Hydrogenolysis results are shown in Table 7.

TABLE 7

| Run No. | Temp. °C. | $CF_3CCl_2CF_3$ % Conv. | $CF_3CHClCF_3$ % Sel. | $CF_3CCl=CF_2$ % Sel. |
|---|---|---|---|---|
| 1 | 210 | 80 | 91 | 9 |
| 2 | 247 | 90 | 85 | 15 |
| 3 | 289 | 96 | 94 | 2 |

EXAMPLE 9

CFC-216aa Hydrogenolysis

The catalyst was 5% Re/C (1.0 g) and the flow rates of $H_2$ and CFC-216aa were 6.5 cc/min and 1 mL/h respectively. Hydrogenolysis results are shown in Table 8.

TABLE 8

| Run No. | Temp. °C. | $CF_3CCl_2CF_3$ % Conv. | $CF_3CHClCF_3$ % Sel. | $CF_3CH_2CF_3$ % Sel. | $CF_3CCl=CF_2$ % Sel. | $CF_3CH=CF_2$ % Sel. |
|---|---|---|---|---|---|---|
| 1 | 177 | 28 | 68 | — | 32 | — |
| 2 | 216 | 64 | 73 | 0.1 | 27 | 0.9 |
| 3 | 245 | 100 | 63 | 2 | 25 | 10 |

EXAMPLE 10

1,2-Dichloro-2,2-difluoroethane (HCFC-132b)

Dehydrohalogenation

The catalyst was 5% Re/C (40.4 g) and the flow rates of $H_2$ and HCFC-132b were 30 cc/min and 3 mL/h. The reaction was carried out at 278° C. and 155 kPa. The reaction product stream, after a run of 53 hours, contained the following compounds (mol%); 71% $CF_2=CH_2$, 0.4% $CH_2=CH_2$, 0.1% $CF_3CH_3$, 0.4% $CF_2HCH_3$, 15% $CF_2ClCH_3$, 0.5% $CF_2=CHCl$, 0.1% $CHF_2CHFCl$, and 12% $CF_2ClCH_2Cl$. The yield of $CF_2=CH_2$ (based on HCFC-132b converted) was 80%.

EXAMPLE 11

HCFC-132b Dehydrohalogenation

The catalyst was 5% Re/C (2.64 g) and the flow rates of $H_2$ and HCFC-132b were 5 cc/min and 2 mL/h. The reaction was carried out at 350° C. and 155 kPa. The reaction product stream contained 35% $CF_2=CH_2$ and 64% HCFC-132b. The reacton was repeated using 2X the hydrogen (10 cc/min) and the following was found in the product stream; 27% $CF_2=CH_2$ and 72% HCFC-132b. The temperature was lowered to 300° C. and the reaction repeated using the last set of conditions and a product stream containing 21% $CF_2=CH_2$ and 78% HCFC-132b was found.

EXAMPLE 12

1,2-Dichloro-1,2,3,3,4,4-hexafluorocyclobutane (C-316)

Dehydrohalogenation

The catalyst was 5% Re/C (1.0 g) and the flow rates of $H_2$ and C-316 were 20 cc/min and 1 mL/h respectively. The reaction was done at 300° C. and the products were analyzed by gas chromatography. All the starting material was consumed and only one peak was detected, which by NMR analysis was shown to be perflurocyclobutene produced with 100% selectivity.

EXAMPLE 13

Bromopentafluorobenzene Hydrogenolysis

The catalyst was 5% Re/C (1.0 g) and the flow rates of $H_2$ and bromopentafluorobenzene were 5 cc/min and 1 mL/h respectively. After reaction at 300° C., the products were analyzed by $^{19}F$-NMR and pentafluorobenzne was found with a selectivity of 87%.

EXAMPLE 14

2,4,6-Trifluoro-3,5-dichloropyridine Hydrogenolysis

The catalyst was 5% Re/C (1.0 g) and the flow rates of $H_2$ and a solution of 2,4,6-trifluoro-3,5-dichloropyridine in hexafluorobenzene were 10 cc/min and 1 mL/h respectively. After reaction at 300° C., analysis by $^{19}F$-NMR of the product stream showed a 60% conversion of the starting material to 2,4,6-trifluoro-3-chloropyridine with a selectivity of 93%.

What is claimed is:

1. In a process for the hydrogenolysis of fluorohalocarbons and/or fluorohalohydrocarbons which contain at least one halo group selected from chloro and bromo by reacting the fluoro-halocarbons and/or fluorohalohydrocarbons with a source of hydrogen in the presence of a catalyst, the improvement comprising utilizing a rhenium-containing catalyst selected from the group consisting of (i) catalysts consisting essentially of rhenium, (ii) unsupported catalysts containing at least about 50 percent by weight rhenium with the balance being one or more Group VIII metals, (iii) catalysts consisting essentially of rhenium supported on carbon, alumina, fluorided alumina, aluminum fluoride, or calcium fluoride, and (iv) supported catalysts consisting essentially of one or more Group VIII metals and from 0.1 to 20 percent by weight of rhenium supported on carbon, alumina, fluorided alumina, aluminum fluoride or calcium fluoride, wherein said one or more Group VIII metals total up to 10 percent by weight and rhenium is the major component on said support.

2. The process of claim 1 wherein the rhenium-containing catalyst consists essentially of rhenium.

3. The process of claim 1 wherein the rhenium-containing catalyst consists essentially of at least 50% by weight of rhenium, the balance being selected from at least one Group VIII metal.

4. The process of claim 1 wherein the rhenium-containing catalyst consists essentially of rhenium supported on carbon.

5. The process of claim 1 wherein the hydrogenolysis is conducted at a temperature from about 100° C. to about 400° C.

6. The process of claim 1 wherein the source of hydrogen is present in an amount of at least 0.2 moles per mole of fluorohalocarbons and/or fluorohalohydrocarbons.

7. The process of claim 1 wherein the fluorohalocarbons and/or fluorohalohydrocarbons are selected from at least one of cyclic and acyclic compounds represented by the empirical formula $C_nH_mF_pX_q$, where X is Cl and/or Br; n is an integer from 1 to 10; m is an integer from 0 to 20; p is an integer from 1 to 21; and q is an integer from 1 to 21, provided that $m+p+q=2n+2$ when the compound is acyclic and equals 2n when the compound is cyclic.

8. The process of claim 1 wherein the fluorohalocarbons and/or fluorohalohydrocarbons are at least one selected from 1,1,1-trichloro-2,2,2-trifluoroethane, 1,1,2-trichloro-1,2,2-trifluoroethane, and 1,2-dichloro-2,2-difluoroethane.

9. The process of claim 5 wherein the rhenium-containing catalyst consists essentially of rhenium.

10. The process of claim 5 wherein the rhenium-containing catalyst consists essentially of at least 50% by weight of rhenium, the balance being selected from at least one Group VIII metal.

11. The process of claim 5 wherein the rhenium-containing catalyst consists essentially of rhenium supported on carbon, alumina, fluorided alumina, aluminum fluoride and/or calcium fluoride.

12. The process of claim 5 wherein the the rhenium-containing catalysts is a supported catalyst consisting essentially of one or more Group VIII metals and rhenium supported on carbon.

13. The process of claim 5 wherein the source of hydrogen is present in an amount of at least 0.2 moles per mole of fluorohalocarbons and/or fluorohalohydrocarbons.

14. The process of claim 5 wherein the fluorohalocarbons and/or fluorohalohydrocarbons are selected from at least one of cyclic and acyclic compounds represented by the empirical formula $C_nH_mF_pX_q$, where X is Cl and/or Br; n is an integer from 1 to 10; m is an integer from 0 to 20; p is an integer from 1 to 21; and q is an integer from 1 to 21, provided that $m+p+q=2n+2$ when the compound is acyclic and equals 2n when the compound is cyclic.

15. The process of claim 5 wherein the fluorohalocarbons and/or fluorohalohydrocarbons are at least one of 1,1,1-trichloro-2,2,2-trifluoroethane, 1,1,2-trichloro-1,2,2-trifluoroethane and 1,2-dichloro-2,2-difluoroethane.

16. The process of claim 1 wherein at least one of the fluorohalocarbons and/or fluorohalohydrocarbons contains chlorine and wherein the product of the reaction comprises at least one fluorohalocarbon and/or fluorohalohydrocarbon containing one less chlorine than the fluorohalohydrocarbon or fluorohalocarbon from which it was formed.

17. The process of claim 1 wherein said fluorohalocarbons and/or fluorohalohydrocarbons are fluorohalohydrocarbons.

18. The process of claim 17 wherein the rhenium-containing catalyst consists essentially of rhenium.

19. The process of claim 17 wherein the rhenium-containing catalyst consists essentially of at least 50% by weight of rhenium, the balance being selected from at least one Group VIII metal.

20. The process of claim 17 wherein the rhenium-containing catalyst consists essentially of rhenium supported on carbon, alumina, fluorided alumina, aluminum fluoride and/or calcium fluoride.

21. The process of claim 17 wherein the hydrogenolysis is conducted at a temperature from about 200° C. to about 400° C.

22. The process of claim 17 wherein the source of hydrogen is present in an amount of at least 0.2 moles per mole of fluorohalocarbons and/or fluorohalohydrocarbons.

23. The process of claim 17 wherein the fluorohalohydrocarbons are selected from at least one of cyclic and acyclic compounds represented by the empirical formula $C_nH_mF_pX_q$, where X is Cl and/or Br; n is an integer from 1 to 10; m is an integer from 1 to 20; p is an integer from 1 to 21; and q is an integer from 1 to 21, provided that $m+p+q=2n+2$ when the compound is acyclic and equals $2n$ when the compound is cyclic.

24. In a process for the hydrogenolysis of fluorohalocarbons and/or fluorohalohydrocarbons which contain at least one halo group selected from chloro and bromo by reacting the fluorohalocarbons and/or fluorohalohydrocarbons with a source of hydrogen in the presence of a catalyst, the improvement comprising utilizing a rhenium-containing catalyst selected from the group consisting of (i) catalysts consisting essentially of rhenium supported on fluorided alumina and/or aluminum fluoride, and (ii) supported catalysts consisting essentially of one or more Group VIII metals and from 0.1 to 20 percent by weight of rhenium supported on fluorinated alumina and/or aluminum fluoride, wherein said one or more Group VIII metals total up to 10 percent by weight and rhenium is the major component on said support.

25. The process of claim 24 wherein the catalyst consists essentially of rhenium supported on fluorinated alumina and/or aluminum fluoride.

26. The process of claim 1 wherein the fluorohalocarbons and/or fluorohalohydrocarbons are selected from the group of fluorohalocarbons consisting of $CCl_2FCClF_2$, $CCl_2FCF_3$ and $CF_3CCl_2CF_3$.

27. The process of claim 26 wherein the fluorohalocarbon is $CCl_2FCF_3$.

28. The process of claim 26 wherein the fluorohalocarbon is $CF_3CCl_2CF_3$.

29. The process of claim 26 wherein the fluorohalocarbon is $CCl_2FCClF_2$.

30. The process of claim 1 wherein the rhenium-containing catalyst consists essentially of rhenium supported on carbon, alumina, fluorided alumina, aluminum fluoride and/or calcium fluoride.

* * * * *